United States Patent [19]

Weinstein

[11] Patent Number: 5,424,265
[45] Date of Patent: Jun. 13, 1995

[54] CAPSULE FOR ABSORBING LIQUID WASTE IN A SUCTION CANISTER

[75] Inventor: Marshall A. Weinstein, East Amherst, N.Y.

[73] Assignee: Safetec of America, Buffalo, N.Y.

[21] Appl. No.: 77,137

[22] Filed: Jun. 15, 1993

[51] Int. Cl.⁶ .................... B01J 20/00; B01D 24/00; B01D 39/00
[52] U.S. Cl. .................. 502/400; 210/282; 210/502.1
[58] Field of Search ............... 502/400; 210/282, 502.1

[56] References Cited

U.S. PATENT DOCUMENTS

| | | | |
|---|---|---|---|
| 3,683,589 | 8/1972 | Seitz et al. | 55/62 |
| 4,816,162 | 3/1989 | Rosskopf et al. | 210/651 |
| 5,206,219 | 4/1993 | Desai | 514/3 |

Primary Examiner—Anthony McFarlane
Assistant Examiner—Nhat D. Phan
Attorney, Agent, or Firm—Phillips, Lytle, Hitchcock, Blaine & Huber

[57] ABSTRACT

A capsule for absorbing liquid waste which contains a a capsule body, a capsule cap joined to said capsule body, and a powder disposed within said capsule. The body of the capsule consists essentially of water-soluble material. Each of the capsule cap and the capsule body contains a domed-shape end section and a linear body section, each of which contains several orifices. The density of orifices in the domed-shape sections exceeds the density of the orifices in the linear body sections. Disposed within the capsule is a powdered absorbent material.

20 Claims, 3 Drawing Sheets

CAPSULE FOR ABSORBING LIQUID WASTE IN A SUCTION CANISTER

FIELD OF THE INVENTION

A degradable capsule for absorbing liquid waste located within a suction canister.

BACKGROUND OF THE INVENTION

Medical waste material, which often contains blood., urine, other body fluids, water, saline solution, iodine or other cleansing materials, are frequently collected in a suction canister system. These systems are well known to those skilled in the art. By way of illustration, one such system is sold by Abbott Laboratories of Abbott Park, Ill.

The Occupational Safety and Health Administration (OSHA) has promulgated regulations relating to the occupational exposure to blood-borne pathogens; see, e.g., 29 Code of Federal Regulations, Part 1910.1030. These regulations mandate that all blood and body fluids must be considered as being contaminated and, consequently, must be treated in a manner sufficient to contain and disinfect any possible, spill, leaking, misting, or spattering.

Thus, there is a need for a fast and efficient means of treating, disinfecting, and insuring the safe handling of liquid medical waste collected within the suction canisters.

Safetec of America Inc., of 1333 Strad Avenue, North Tonawanda, N. Y., disclosed a process for encapsulating liquid medical waste within a suction canister in their Spring, 1993 catalog; at the last page of this catalog, it is disclosed that one may pour "Red Z" encapsulating powder into the suction canister to form a gelatinous mass which may be readily and safely be disposed of. Once the liquid medical waste has been converted to a gelatinous form, both the suction canister and the gel-like material in it may be disposed of by, e.g., burying it in a sanitary landfill, or incineration. The conversion of the liquid waste into a less fluid gel form renders it safer to handle.

In the prior art waste disposal system, the "Red Z" powder is often dispensed from a plastic film packet one of whose ends may be opened prior to the dispensing. During such dispensing, it is often difficult to estimate precisely how much absorbent powder should be poured into the suction canister; after such dispensing, in addition to having to dispose of the suction canister assembly, one also must dispose of a plastic film packet which, often, still contains some absorbent material.

Furthermore, the prior art systems frequently take a relatively long period of time before the entire mass of waste liquid is converted to a gelatinous mass.

It is an object of this invention to provide a device which will convert a specified amount of liquid waste into a gelatinous mass and, after such conversion, will be totally consumed.

It is another object of this invention to provide a degradable capsule containing both an absorbent and a biocidal material.

It is yet another object of this invention to provide a degradable capsule containing an absorbent material whose ends will degrade prior to the main portion of its body.

It is another object of this invention to provide a degradable capsule which will immobilize a specified amount of liquid waste in a substantially shorter period of time than comparable prior art devices.

It is yet another object of this invention to provide a degradable capsule which, after contact with the liquid medical waste, will first sanitize such liquid waste prior to the time it substantially immobilizes it.

It is another object of this invention to provide a time-release degradable capsule.

It is another object of this invention to provide a novel composition especially suited to be used within such degradable capsule.

It is another object of this invention to provide a process for preparing such novel composition.

SUMMARY OF THE INVENTION

In accordance with this invention, there is provided a degradable capsule, containing a multiplicity of holes in its exterior surface, which is comprised of a powdered absorbent material. When such capsule is contacted with liquid medical waste, it will float on the top surface of the liquid waste.

BRIEF DESCRIPTION OF THE DRAWINGS

The present invention will be more fully understood by reference to the following detailed description thereof, when read in conjunction with the attached drawings, wherein like reference numerals refer to like elements, and wherein.

DESCRIPTION OF THE PREFERRED EMBODIMENT

Figure 1:
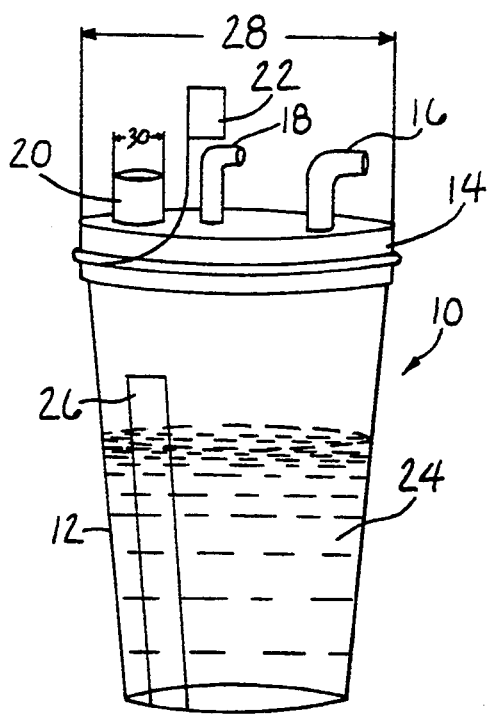
FIG. 1 is a schematic side elevation of a typical suction canister containing liquid medical waste which may be used in conjunction with applicant's novel capsule.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., cross-hatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

FIG. 1 is a perspective view of a typical suction canister 10 comprised of a container 12, a lid 14, a vacuum fitting 16, a patient fitting 18, a port hole 20, and a cover 22 for port hole 20. In typical operation of this device, vacuum fitting 16 is connected to a source of vacuum (not shown), and patient fitting 18 is connected to the source of the medical waste (such as, e.g., blood from a surgical site) by means, e.g., of a tube (not shown); the liquid medical waste 24 is thereby deposited within container 12 of canister 10.

The suction canister 10 illustrated in FIG. 1, and similar receptacles for the receipt of medical waste, are well known to those skilled in the art.

By way of illustration, U.S. Pat. No. 5,002,534 (the disclosure of which is hereby incorporated by reference into this specification) discloses an aspirator including a container having an internal chamber, the chamber having a suction tube connected to a closed bellows within the chamber, and also having a patient tube for insertion into the body cavity of a patient for sucking removal of mucous and other body fluids.

By way of further illustration, one may use one or more of the devices described in U.S. Pat. Nos. 5,100,376, 5,098,418 (comprised of a squeeze bulb for hand actuation), 5,084,013 (surgical suction tube), 5,083,561 (tracheal suction catheter), 5,073,164 (suction catheter), 5,052,403 (self-contained blood collection system), 5,045,077, 5,045,075, 5,034,006 (suction equipment for medical operation), 5,032,184 (movable suction head), 5,026,358 (drainage device), 5,014,389 (foot manipulated suction head), 5,011,470 (combined surgical drainage and autotransfusion device), and the like. The entire disclosure of each of these United States patents is hereby incorporated by reference into this specification.

Suction canisters similar to those depicted as element 10 in FIG. 1 are well known to those skilled in the art. Thus, for example, one may purchase such suction canisters 10 as the "Bemis Suction Canister System" (Bemis Bag Company of Chicago, Ill.), the "Handi-Vak II Disposable Collection System" (Allied Healthcare Products, Inc. of Long Island, N.Y., and the like.

Referring again to FIG. 1, and the preferred embodiment of the suction canister 10 depicted therein, it will be seen that container 12 preferably is comprised of a scale 26 which usually is printed on the outside of container 12. This scale allows one to determine the volume of the medical waste 24 within container 12.

Referring again to FIG. 1, and in the preferred embodiment illustrated therein, lid 14 preferably has a substantially circular cross-section with a diameter 28 of from about 5.5 to about 7.5 inches. In general, in this embodiment, port hole 20 has an internal diameter of from about 0.8 to about 1.3 inches. Container 12 generally has a volume ranging from about 800 to about 3,200 cubic centimeters.

Figure 2:
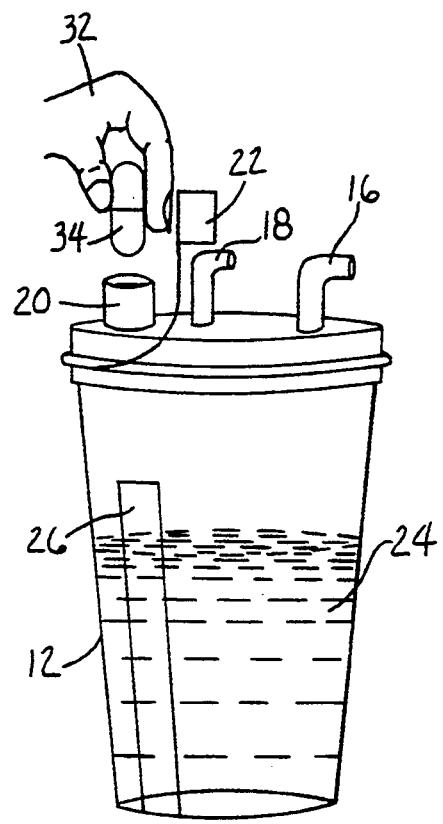
FIG. 2 is a schematic side elevation of a user inserting one preferred capsule of this invention into the suction canister of FIG. 1.

FIG. 2 illustrates a user 32 depositing one preferred capsule 34 of this invention into the canister through porthole 20. As will be apparent to those skilled in the art, capsule 34 will have a maximum width which generally does not exceed about 1.3 inches.

Figure 3:
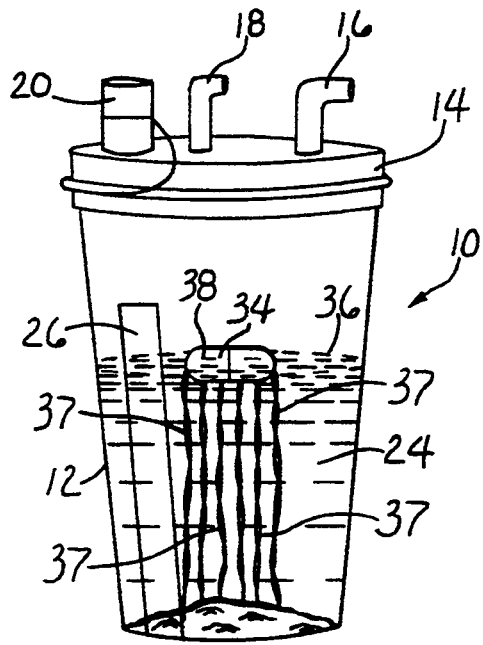
FIG. 3 is a schematic side elevation showing the capsule of FIG. 2 disposed in the suction canister of FIG. 1, and illustrates the initial degradation of such capsule.

FIG. 3 illustrates what happens when capsule 34 is dropped within container 12. Because of its composition and weight, it floats upon the surface 36 of liquid medical waste 24. The shell 38 of capsule 34 contains a multiplicity of holes (not shown in FIGS. 3 and 4) which allow the material 37 within capsule 34 to stream downwardly towards the bottom of container 12 while interacting with the liquid waste 24 within such container.

Figure 4:
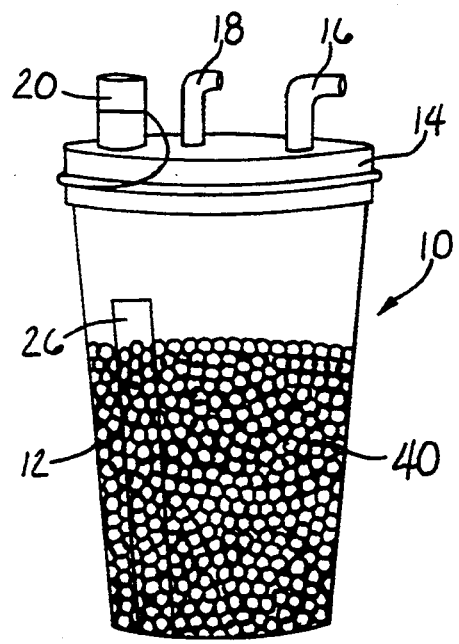
FIG. 4 is a schematic side elevation showing the capsule of FIG. 2 disposed within and the suction canister of FIG. 1, and illustrates the complete degradation of such capsule within such canister.

FIG. 4 illustrates what happens when capsule 34 has been within container 12 for a time sufficient to allow it to completely degrade. At this time, all of its contents have escaped from the capsule 34 (which no longer exists), and the contents have interacted with the liquid medical waste to form a gelatinous mass 40 which is readily easy to handle. In this regard, note that the aforementioned OSHA Standard (29 C.F.R., Part 1910.1030) requires that " . . . all procedures involving blood or potentially infectious materials shave be performed in a manner as to minimize splashing, spraying, spattering and generation of droplets of these substances . . . Collection vessels should not permit blood or other potentially infectious fluid to pass through, spill or mist . . . under normal conditions of use and for the duration of time the vessel is used." The fine for violation of this Standard is seven-thousand dollars per occurrence.

Figure 5:
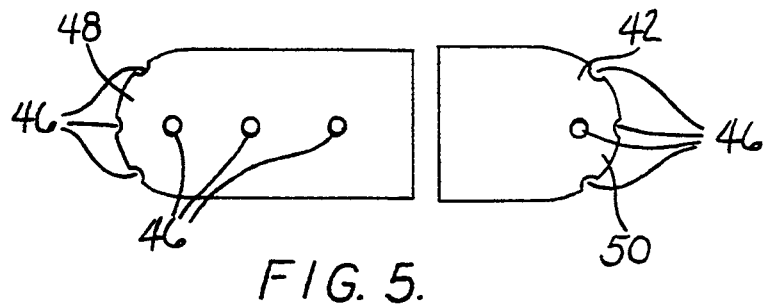
FIG. 5 is a side elevation showing the components of the capsule of FIG. 2.

FIG. 5 is a side elevation view of the components of one preferred embodiment of capsule. Referring to FIG. 5, it will be seen that, in the preferred embodiment illustrated therein, the capsule 34 is comprised of cap 42 and body 44, the cap 42 being adapted to fit over body 44 (see FIG. 8).

Both the cap 42 and the body 44 preferably consist essentially of a water-soluble material adapted to allow the capsule 34 to degrade while in water. Any suitable water-soluble material may be used in these components.

By way of illustration and not limitation, one may use the water-soluble graft polymer of alkyl acrylate on a polvinyl alcohol/polyvinyl acetate copolymer, which is disclosed in U.S. Pat. No. 3,300,546 of Baechtold, the entire disclosure of which is hereby incorporated by reference into this specification.

By way of further illustration, one may use a blend of hydroxybutylmethylcellulose and hydroxyproprylmethylcellulose to make the capsule; see, e.g., U.S. Pat. No. 4,765,916 of Ogar, the entire disclosure of which is hereby incorporated by reference into this specification.

By way of yet further illustration, one may use the materials described in one or more of U.S. Pat. Nos. 2,560,649, 3,346,502 (polyvinyl acetate), 3,525,426 (water-soluble geltain), 3,528,921 (polyvinyl alcohol), 3,534,851, 3,556,765, 3,634,260 (polyvinyl alcohol), 3,671,439, 3,706,670, 3,857,195, 3,877,928, 4,367,156, 4,747,976, and the like. The entire disclosure of each of these patents is hereby incorporated by reference into this specification.

In one preferred embodiment, the cap 42 and the body 44 of capsule 34 each preferably consist essentially of gelatin material. In one preferred aspect of this embodiment, each of such components contains from about 80 to about 84 weight percent of gelatin and at least about 10 weight percent of water, and up to about 6 weight percent of other ingredients. Thus, for example, the composition may contain from about 81.6 to about 82.6 weight percent of gelatin, from about 13 to about 14 weight percent of water, about 3 weight percent of propylene glycol, from about 0.6 to about 0.8 weight percent of methylparaben, from about 0.06 to about 0.08 weight percent of propylparaben, and from about 0.1 to about 0.3 weight percent of sodium lauryl sulfate.

Referring again to FIG. 5, it will be seen that, in the preferred embodiment depicted therein (and also in FIGS. 6, 7, and 8), each of the cap 42 and the body 44 is comprised of a multiplicity of holes 46. As is illustrated in such Figures, these holes 46 are preferably disposed over substantially much of the entire surface of cap 42 and body 44.

The diameter of holes 46 may vary from a very small pinprick up to about 0.13 inches in diameter. Although larger diameter holes may also be used, they are not preferred.

Figures 6, 7:
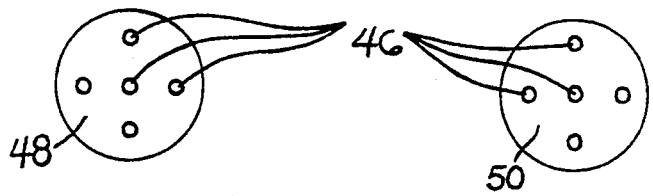
FIG. 6 is a left end view of the capsule of FIG. 2.
FIG. 7 is a right end view of the capsule of FIG. 2.
Figure 8:
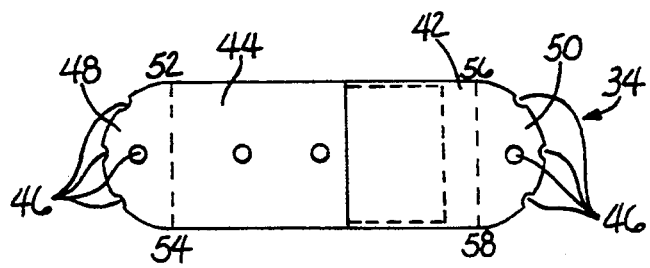
FIG. 8 is a top view of the capsule of FIG. 2.

FIGS. 6 and 7 illustrate the right and left ends, respectively, of cap 42 and body 44. FIG. 8 illustrates the construction of capsule 34, with cap 42 and body 44 being joined in locking relationship.

Gelatin capsule 34 may be constructed by conventional means. Thus, by way of illustration and not limitation, such capsule 34 may be made by the processes of one or more of U.S. Pat. Nos. 4,667,498, 4,990,358, 4,966,771, 4,867,983, and the like. The disclosure of each of these patents is hereby incorporated by reference into this specification.

The gelatin capsule 34 also may be purchased from commercial sources. Thus, e.g., one may purchase such gelatin capsules from Torpac, Inc. of 26 Littell Road, East Hanover, N.J. The Torpac, Inc. capsules are available in sizes which range from a cut length for the cap 42 of from about 19 to about 39 millimeters, a cut length for the body 44 of from about 23 to about 76.8 millimeters, a double wall thickness of from about 0.33 to about 0.39 millimeters, a dome thickness of from about 0.33 to about 0.39 millimeters, an outer diameter of from about 14.6 to about 23.5 millimeters, and a prelocked length of from about 34 to about 91.5 millimeters.

As will be apparent to those skilled in the art, the capsule 34 may, but need not, have a substantially circular cross-section over its entire length. What is essential, however, is that it must contain a first arcuate end section 48 (a first "domed" section), and a second arcuate end section 50.

Referring to FIG. 8, it will be seen that the first arcuate dome section 48 extends from point 52 to point 54, and that the second arcuate dome section 50 extends from point 56 to point 58.

In general, the dome of cap 42 is larger than the dome of body 44, and the combined length of such two dome sections is no greater than about 25.0 percent of the total length of capsule 24. Notwithstanding this, the total number of orifices 46 present in dome section 48 and in dome section 50 exceed the total number of orifices present in the remainder of the capsule 34.

In one embodiment, each of domed sections 48 and 50 contain at least five orifices 46 equally disposed therein; and the remainder of the body of the capsule 34 contains at least 8 such orifices equally disposed around such body at 1.0 inch distances, provided that the total number of orifices in the domed sections exceeds the total number of orifices in the body by at least about 2.

The orifices may be produced into cap 34 and body 42 sections by conventional means. Thus, for example, during the manufacture of such parts they may be molded therein by the dipping process referred to in U.S. Pat. Nos. 4,674,498, 4,990,358, 4,966,771, and 4,867,983.

In one preferred embodiment, after cap 34 and body 42 are produced with the required number of orifices therein, these orifices are sealed by applying to cap 34 and body 42 a water-soluble polyvinyl alcohol material which fill the orifices and prevent absorbent material from passing therethrough until the capsule 34 is contacted with an aqueous medium.

The sealed body 42 may then be filled with absorbent powder and attached to cap 34 by conventional means. Thus, one may use a "Manually Operated Capsule Filling Machine" sold by the Pam Pharmaceutical and Allied Machinery Company Pvt. Ltd. of 127, Kandivli Industrial Estate, Kandivli (West), Bombay, India as model number MF30. Thus, e.g., one may use an "ACTA-fill 800" semi-automatic capsule filling machine which is sold by the Acta Pharmacal Company of 380 San Aleso Avenue, Sunnayvale, Calif. Other well-known conventional means of producing such filled capsule 34 also may be used.

In one preferred embodiment, after the body portion 44 of capsule 34 has been formed, it is filled with the preferred absorbent composition of this invention, the cap 42 is then lockably inserted over it, and a multiplicity of orifices 46 are then formed in the capsule parts 42 and 44. Thereafter, in one preferred aspect of this embodiment, the orifices 46 are filled with a water-soluble sealant such as, e.g., polyvinyl alcohol such as the polyvinyl alcohol materials described in patents listed elsewhere in this specification.

Referring again to FIG. 9, when capsule 34 is first inserted through porthole 20 (not shown), it rights itself and floats on the surface of liquid waste 24.

Figure 9:
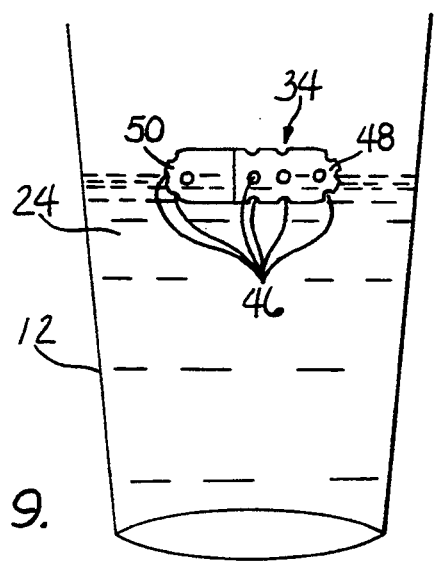
FIGS. 9, 10, and 11 are each a partial sectional view of the capsule of FIG. 2 floating in the liquid medical waste of a suction canister, showing such capsule being degraded to different extents.

As will be seen by reference to FIG. 9, about half of capsule 34 is submerged in liquid 24 while it is floating thereon. The half of the capsule 34 which is contacted with such aqueous liquid starts to degrade.

Because the polyvinyl alcohol material degrades faster than the gelatin material, the plugged orifices 46 are more likely to allow the escape of absorbent material than is the gelatin body of the capsule 34.

Figure 10:
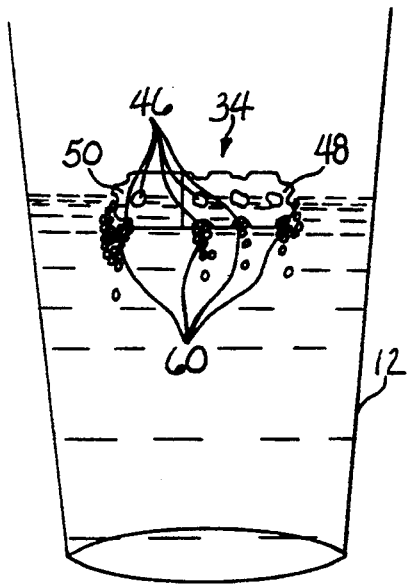

FIG. 10 illustrates the results of this differential in water solubility. Absorbent particles 60 start flowing from the formerly plugged orifices 46 which are in contact with the aqueous media.

Because the number of holes in the domed areas 48 and 40 is greater than the number of holes in the body of the capsule, and because of the density of the plugged holes 46 in the domed areas 48 and 50 is also substantially higher than the density of the plugged holes 46 in the body of capsule 34, substantially more of absorbent particles 60 flow from the domed areas 48 and 50 than flow from the body of capsule 34.

Figure 11:
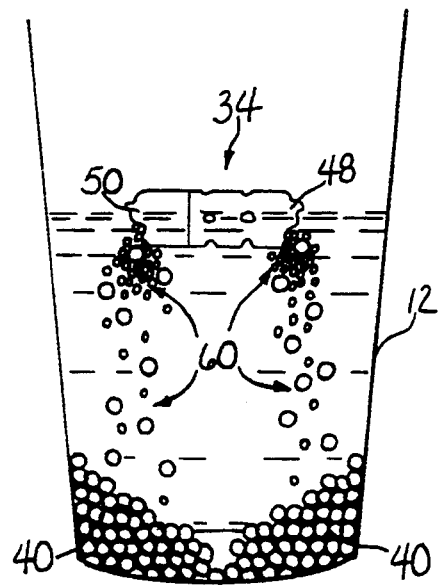

The results of this differential degradation of the capsule is illustrated in FIG. 11. As the mass of absorbent particles 60 come pouring out of the domed areas 50 and 48 of the capsule 34, the interact with the aqueous medium 24 and, ultimately, form a gelatinous mass 62. One may also refer to FIG. 4 for an illustration of this phenomenon, FIG. 12 illustrates one preferred capsule 34 which takes advantage of the phenomenon described above to first disinfect the aqueous medium 24 prior to the time the mass of absorbent material is contacted with it.

Figure 12:
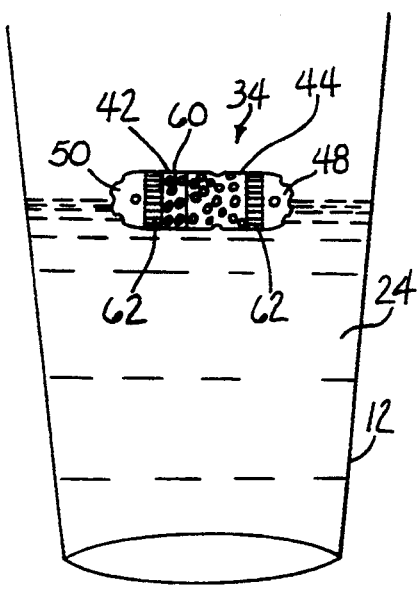
FIG. 12 is a sectional view of another preferred capsule of this invention.

Referring to FIG. 12, it will be seen that, in the preferred embodiment illustrated in it, cap 42 and body 44 are each filled in such a manner that a biocidal material 62 is disposed within or near the domed areas 48 and 50. Consequently, because these areas tend to degrade more readily than the rest of the capsule 34, the majority of biocidal material 62 is contacted with aqueous media 24 prior to the time that the majority of the absorbent particles 60 are contacted with such media.

In the embodiment illustrated in FIG. 12, the biocidal material is in tablet form. As will be apparent to those skilled in the art, such biocidal material may be in other forms such as, e.g., a powder form.

The biocidal material is readily available. Thus, for example, one may purchase chlorine-generating tablets from the Olin Corporation of Niagara Falls, N.Y.; many of these tablets are commonly used to treat swimming pools and to chlorinate water.

Other biocides which are commercially available also may be used. Thus, by way of further illustration, one may purchase powdered biocidal material from the vendors listed on page 129 of "The 1993 CPI Purchasing Chemicals Yellow Pages" (CPI Purchasing, 275 Washington Street, Newton, Mass. 02158).

By way of further illustration, one may use a chlorine-generating material solid sold under the trademark of "ACL" by the Monsanto Corporation of 800 North Lindbergh Road, St. Louis, Mo. Thus, one may use trichloro(iso)cyanuric acid ("ACL 90 PLUS"), and/or sodium dichloro(iso)cyanurate ("ACL 60), and/or potassium dihchloro(iso) cyanurate ("ACL 59), and/or sodium dichloro(iso)cyanurate dihydrate ("ACL 56).

By way of further illustration, one may use a 2-benzyl-4-chlorophenol composition sold by the Dow Chemical Corporation of Midland, Mich. under the tradename of "DOWCIDE."

The capsule 34 is preferably filled with a powder composition, substantially all of whose particles are smaller than about 50 microns.

At least about 50 weight percent of the powder mixture within capsule 34 is comprised of an absorbent. It is preferred that at least about 80 weight percent of such powder mixture be an absorbent. It is more preferred that at least about 90 weight percent of said powder mixture be an absorbent.

One may use any of the absorbents well known to those skilled in the art.

Thus, e.g., one may use the water-absorbing alkali metal carboxylate salts of starch-polyacrylonitrile graft copolymers disclosed in U.S. Pat. No. 3,661,815, the entire disclosure of which is hereby incorporated by reference into this specification. One may also use the similar copolymeric materials disclosed in U.S. Pat. No. 3,932,322, 3,997,484, and 4,192,727, the disclosure of which are also incorporated by reference into this specification.

One may also use organic polymers in which hydrophilic groups constitute from 25 to 72 percent of the molecular structure and the polymeric network is lightly cross-linked; these materials often have a minimum average molecular weight per cross-linkage of about 13,000 and a maximum molecular weight per cross-linkage of about 276,000. These materials are often referred to as "hydrogels," "hydrocolloid polymers," "superabsorbents," and the like; and they are discussed in U.S. Pat. No. 4,449,977, the entire disclosure of which is hereby incorporated by reference into this specification.

By way of further illustration, one may use one or more of the hydrogels disclosed in U.S. Pat. Nos. 4,076,663, 4,286,082, 3,670,731, 3,664,343, 3,783,871 and in Belgian patent 785,858; the disclosure of each of these patents is hereby incorporated by reference into this specification.

By way of further illustration, one may use the water swellable and water absorbent polymers described in U.S. Pat. Nos. 4,685,420, 3,699,103, 3,686,034, 3,758,641, 3,810,468, 3,900,030, 3,926,891, 3,954,821, 3,959,569, 3,966,679, 3,980,663, 3,983,095, 3,989,586, 3,993,616, 4,008,353, 4,017,653, 4,018,951, 4,026,932, 4,041,020, 4,041,228, 4,041,231, 4,056,502, 4,057,521, 4,061,846, 4,071,650, 4,076,673, 4,076,928, 4,079,029, 4,132,695, 4,154,898, 4,186,233, 4,293,609, 4,424,247, 4,435,172, 4,444,830, 4,459,068, 4,486,374, 4,500,585, 4,500,670, 4,511,477, 4,526,240, 4,529,739, 4,535,098, 4,725,465, 4,985,023, 5,091,443, and the like; the entire disclosure of each of these patents is hereby incorporated by reference into this specification.

In one preferred embodiment, the absorbent material is a potassium polyacrylate polymeric material comprised of a repeating structural unit of the formula ($C_3H_3O_2K$) which is obtained from the Stockhausen, Inc. of 2408 Doyle Street, Greensboro, N.C. as "FAVOR SAB 800." This material has a particle size of from about 100 to about 850 microns, and a density of from about 500 to about 600 grams per liter.

Without wishing to be bound to any particular theory, applicant believes that the carboxylic groups of FAVOR SAB 800 are solvated when brought into contact with water or water-based liquid and, thus, partially dissociate into negatively charged carboxylic ions. In this state, the polymer chain contains a large number of similarly charged ionic groups which repel each other. The polymer coils become more bulky and thus extend their propensity to absorb increasing quantities of the aqueous liquid. This process would normally lead to a complete solution of the polymer. However, due to the cross-linking between the polymer chains of FAVOR SAB 800 super absorbent polymer, only the formation of a gel takes place, precluding its solution. The water is strongly bonded by means of hydrogen bonds in the gel.

In addition to the absorbent material, the powder within capsule 34 also preferably (but not necessarily) is comprised of up to about 50 weight percent of an antimicrobial agent. In one embodiment, less than about 5.0 weight percent of the mixture within capsule 34 is comprised of such antimicrobial agent. In another embodiment, from about 1 to about 3 weight percent of the antimicrobial agent is present in the mixture.

Any of the disinfectants in solid form which are known to those skilled in the art may be used. Thus, e.g., one may use one or more of the disinfectants disclosed in U.S. Pat. Nos. 4,842,853, 4,993,084, 5,036,077, 5,089,228, and the like; the disclosure of each of these patents is hereby incorporated by reference into this specification.

In one preferred embodiment, where the biocidal material is a chlorine-generating material, it is preferred to coat the surface of the biocidal grains to prevent the surface thereof from contacting the particles of absorbent prior to the time the entire composition is contacted with aqueous medium. Applicant has discovered that, unless such coating step is used, the long term activity of the absorbent composition sometimes suffers.

In one preferred embodiment, a microcrystalline cellulose material sold under the tradename of "EMOCEL 90M" by the Edward Mendell Company, Inc. of Route 52, Carmel, N.Y. is used. In another preferred embodiment, a microcrysalline cellulose material sold under the tradename of "AVICEL PH 102" by the Food Machinery Corporation of 2000 Market Street, Philadelphia, Pa., is used. Other suitable coating materials which are well known to those skilled in the art also may be used.

It is preferred to mix from about 10 to about 20 weight of coating material and from about 80 to 90 weight percent of chlorine-generating biocidal material to produce the coated biocide. When calculating the amount of biocide in applicant's composition, in this embodiment the weight of the coated chlorine-containing biocide is used.

In one embodiment, less than from about 0.1 to about 0.9 weight percent of surfactant, by total weight of absorbent composition, is used in applicant's composition. In this embodiment, it is preferred to use at least one anionic surfactant and, more preferably, at least two anionic surfactants.

In one embodiment, the surfactant used a sodium lauryl sarcosinante sold under the tradename of "VANSEAL NALS-95" by the R. T. Vanderbilt Company, Inc. of 30 Winfield Street,. Norwalk, Conn. In another embodiment, the surfactant used is another sodium lauroyl sarcosinate sold under the name of "VANSEAL NALS-30" by the R. T. Vanderbilt Company, Inc. In yet another embodiment, a mixture of these two surfactants is used.

In one preferred embodiment, applicant's composition also contains from about 0.01 to about 1.5 weight percent of a disintegrant which, upon contact of the composition water, will facilitate the dissolution of the powders within the capsule. Disintegrant materials are well known to those skilled in the art; and any of the conventional ones may be used in applicant's composition.

Thus, by way of illustration and not limitation, one may use one or more of the distintegrants described in U.S. Pat. Nos. 5,098,907 (nonionic surfactant), 5,084,277 (cornstarch), 5,064,656, 4,999,2000 (calcium carbonate), 4,970,078 (carboxymethylguar), 4,950,484 (hydroxypropylcellulose), 4,904,477, 4,886,669, 4,867,987, 4,853,437, 4,631,305, 4,086,335 (chitin), 4,072,535, 3,622,677 (compacted starch), and the like. The disclosure of each of these United States Patents is hereby incorporated by reference into this specification.

In one preferred embodiment, the disintegrant used is a sodium starch glycolate sold under the name of "EXPLOTAB" by the Edward Mendell Company of 2981 Route 11, Patterson, N.Y. 12563.

Figure 13:
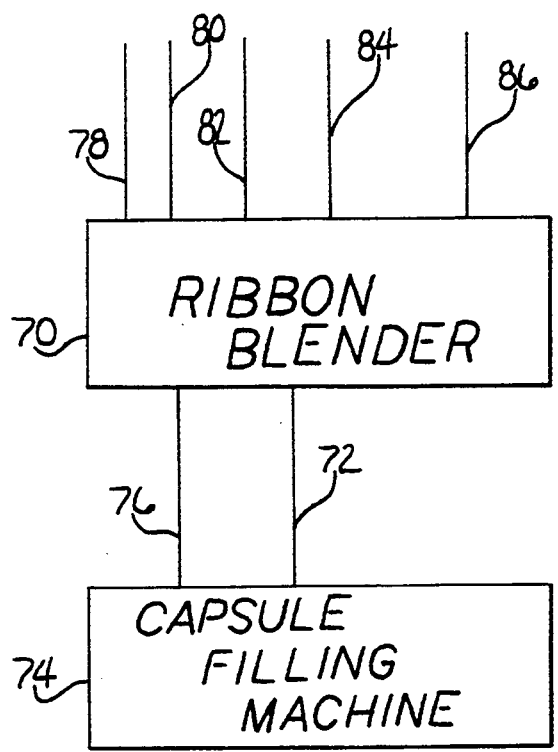
FIG. 13 is a flow chart illustrating the preparation of one preferred composition used in the capsule of this invention.

FIG. 13 is a flow chart illustrating one preferred process for producing the composition of this invention. Referring to FIG. 13, and to the preferred embodiment depicted therein, it will be seen that it is preferred to first blend the ingredients in mixer 70 and thereafter charge the mixed composition via line 72 to capsule filling machine 74. Capsule components 42 and 44 (not shown) may be charged to capsule filling machine 74 via line 76, and the filled capsule 34 (not shown) may be constructed in such machine.

Referring again to FIG. 13, it is preferred to charge about 3.0 parts (per 100 parts of total composition) of the "ACL 60" chlorine-generating biocide to mixer 70 via line 78. Thereafter, from about from 10 to about 20 weight percent of "EMCOCEL" microcrystalline cellulose (by total weight of microcrystalline cellulose and biocide) is charged to the mixer 70. Thereafter, mixing occurs for at least about five minutes until a substantially homogeneous mixture is produced.

Any of the mixers known to those skilled in the art may be used to mix applicant's composition. Thus, e.g., one may use one or more of the mixers described on pages 19-4 to 19-26 of Robert H. Perry et al.'s "Chemical Engineers Handbook," Fifth Edition (McGraw Hill Book Company, New York, 1973). Thus, e.g., one may use a ribbon blender.

After the biocide has been coated within mixer 70, from about 0.1 to about 1.5 parts (per hundred parts of total composition) of one or more surfactants is added via line 82. It is preferred to add from about 0.1 to about 0.6 parts of surfactant, per 100 parts of total composition. In one embodiment, one or more anionic surfactants (such as "VANSEAL NALS-95" and/or "VANSEAL NALS-30") is used.

A disintegrant is added via line 84. This disintegrant may be added after the addition of the surfactant, or it may be added prior to the addition of the surfactant. It is preferred, however, that neither ingredient be added prior to the coating of the biocide. It is also preferred to add the absorbent after each of the other ingredients has been charged to the mixer.

From about 0.05 to about 1.0 part (per hundred parts of total composition) of the disintegrant are charged via 3Line 84. It is preferred to charge from about 0.3 to about 0.7 parts of disintegrant (per hundred parts of composition). One preferred disintegrant is sodium starch glcyolate.

It is preferred to charge the absorbent to the mixer 70 via line 86 after all of the other ingredients have been charged. However, the absorbent may be charged prior to the charge of the other ingredients, provided that the absorbent is mixed with a coated biocide when the biocide used generates chlorine upon contact with aqueous media.

It is preferred to charge at least about 95 parts of the absorbent per hundred parts of total composition. The preferred absorbent is a potassium polyacrylate copolymeric composition sold as "FAVOR SAB 800."

The absorbent and the other ingredients are preferably dry mixed until a substantially homogeneous composition is obtained. Thereafter, this composition is charged via line 72 to capsule filling machine 74.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

In one embodiment, the capsule 34 is comprised or microporous orifices so small that they cannot generally be perceived by a naked eye. These orifices may be made in the capsule 34 by electrostatic means.

Therefore, while several preferred forms of the inventive capsule have been shown and described, and several modifications thereof discussed, persons skilled in this art will readily appreciate that various additional changes and modifications may be made without departing from the spirit of the invention, as defined and differentiated by the following claims.

What is claimed is:

1. A capsule for absorbing liquid waste comprised of a capsule body, a capsule cap joined to said capsule body, and a powder disposed within said capsule, wherein:
   (a) said capsule body consists essentially of water-soluble material;
   (b) said capsule cap consists essentially of water-soluble material;
   (c) said capsule body is comprised of a first substantially domed-shape end section integrally connected to a first substantially linear body section;
   (d) said capsule cap is comprised of a second substantially dome-shaped end section integrally connected to a second substantially linear body section;
   (e) each of said first substantially dome-shaped end section, said second substantially dome-shaped end section, said first substantially linear body section, and said second substantially linear body section is comprised of a multiplicity of orifices, wherein:
      (i) the number of said orifices in said first substantially dome-shaped end section and said second substantially dome-shaped end section exceeds the number of said orifices in said first substantially linear body section and said second substantially linear body section,
      (ii) the density of orifices in said first substantially domed-shaped end section exceeds the density of orifices in said first substantially linear body section, and
      (iii) the density of orifices in said second substantially domed-shape end section exceeds the density of orifices in said second substantially linear body section; and
   (f) said powder is comprised of at least about 50 weight percent of an absorbent.

2. The capsule as recited in claim 1, wherein each of said orifices is coated with a water-soluble material.

3. The capsule as recited in claim 1, wherein said powder is comprised of from about 0.5 to about 15 weight percent of a biocide.

4. The capsule as recited in claim 1, wherein said powder is comprised of from about 0.01 to about 1.5 weight percent of a disintegrant.

5. The capsule as recited in claim 1, wherein said powder is comprised of from about 0.0 to about 0.9 weight percent of a surfactant.

6. The capsule as recited in claim 1, wherein said powder is comprised of at least about 80 weight percent of absorbent.

7. The capsule as recited in claim 1, wherein said powder is comprised of at least about 90 weight percent of absorbent.

8. The capsule as recited in claim 7, wherein each of said orifices is coated with a water-soluble material.

9. The capsule as recited in claim 8, wherein said powder is comprised of from about 0.5 to about 15 weight percent of a biocide.

10. The capsule as recited in claim 9, wherein said biocide produces chlorine upon contact with an aqueous medium.

11. The capsule as recited in claim 10, wherein said biocide is coated with a material which does not produce chlorine upon contact with said aqueous medium.

12. The capsule as recited in claim 11, wherein said powder is comprised of from about 0.01 to about 1.5 weight percent of a disintegrant.

13. The capsule as recited in claim 12, wherein said powder is comprised of from about 0.0 to about 0.9 weight percent of a first surfactant.

14. The capsule as recited in claim 13, wherein said first surfactant is an anionic surfactant.

15. The capsule as recited in claim 14, wherein said capsule body and said capsule cap each is comprised of at least about 70 weight percent of gelatin.

16. The capsule as recited in claim 15, wherein said water-soluble material coating each of said orifices has a water-solubility which is greater than the water solubility of gelatin.

17. The capsule as recited in claim 16, wherein said absorbent consists essentially a copolymer of alkali metal polyacrylate.

18. The capsule as recited in claim 17, wherein said alkali metal is potassium.

19. The capsule as recited in claim 18, wherein said copolymer is a starch-polyacrylate graft copolymer.

20. The capsule as recited in claim 19, wherein said disintegrant is sodium starch glycolate.

* * * * *